United States Patent
Lee et al.

(10) Patent No.: US 7,598,223 B2
(45) Date of Patent: Oct. 6, 2009

(54) METHODS FOR PRODUCING TARGET CELL REACTIVE LYMPHOCYTES

(75) Inventors: Peter P. Lee, Menlo Park, CA (US); Tor B. Stuge, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 406 days.

(21) Appl. No.: 11/185,245

(22) Filed: Jul. 19, 2005

(65) Prior Publication Data

US 2006/0029579 A1 Feb. 9, 2006

Related U.S. Application Data

(60) Provisional application No. 60/591,889, filed on Jul. 27, 2004.

(51) Int. Cl.
*A61K 38/00* (2006.01)
*A61K 39/00* (2006.01)

(52) U.S. Cl. ................. 514/15; 424/185.1; 530/328

(58) Field of Classification Search ................. None
See application file for complete search history.

(56) References Cited

OTHER PUBLICATIONS

Thumann, P., et al. Antigen loading of dendritic cells with whole tumor cell preparations. J. Immunol. Methods. 2003. vol. 277, pp. 1-16.*
Mitchell MS., et al. Active specific immunotherapy for melanoma: Phase I trial of allogeneic lysates of a novel adjuvant. Cancer Res. 1988. vol. 48, pp. 5883-5893.*
Sosman JA, et al. Adjuvant immunotherapy of resected, intermediate-thickness, node-negative melanoma with an allogeneic tumor vaccine: Impact of HLA class I antigen expression on outcome. J. Clin. Oncol. 2002. vol. 20, pp. 2067-2075.*
Bullock et al., Antigen Density Presented by Dendritic Cells in vivo Differentially Affects the Number and Avidity of Primary, Memory, and Recall $CD8^+$T Cells[1], The J. of Immunol., 2003, 170: 1822-1829.
Oh et al., Selective Induction of High Avidity CTL by Altering the Balance of Signals From APC, The J. of Immun., 2003, 170: 2523-2530.
Xu et al., Rapid High Efficiency Sensitization of $CD8^+$T Cells to Tumor Antigens by Dendritic Cells Leads to Enhanced Functional Avidity and Direct Tumor Recognition Through an IL-12-Dependent Mechanism[1], The J. of Immun., 2003, 171: 2251-2261.
Marchand et al., Biological and clinical developments in melanoma vaccines, Ashley Publications Ltd., 2001, 1451-2598.
Rammensee et al., Molecular Biology Intelligence Unit-MHC Ligands and Peptide Motifs, Landes Bioscience, 1997, Springer-Verlag, Heidelberg, Germany.

* cited by examiner

*Primary Examiner*—Robert Landsman
*Assistant Examiner*—Bruce D Hissong
(74) *Attorney, Agent, or Firm*—Bozicevic, Field & Francis LLP; Pamela J. Sherwood

(57) ABSTRACT

Methods and compositions for producing target cell reactive lymphocytes, e.g., cytolytic T-lymphocytes, in a subject are provided. In practicing the subject methods, a lymphocyte population is contacted with an effective amount of a target cell peptide mixture of active and inactive peptides to produce lymphocytes reactive, e.g., cytolytic, for the target cell. Also provided are compositions, kits, and systems for practicing the subject methods. The subject invention finds use in a variety of different applications, including therapeutic applications.

1 Claim, 12 Drawing Sheets

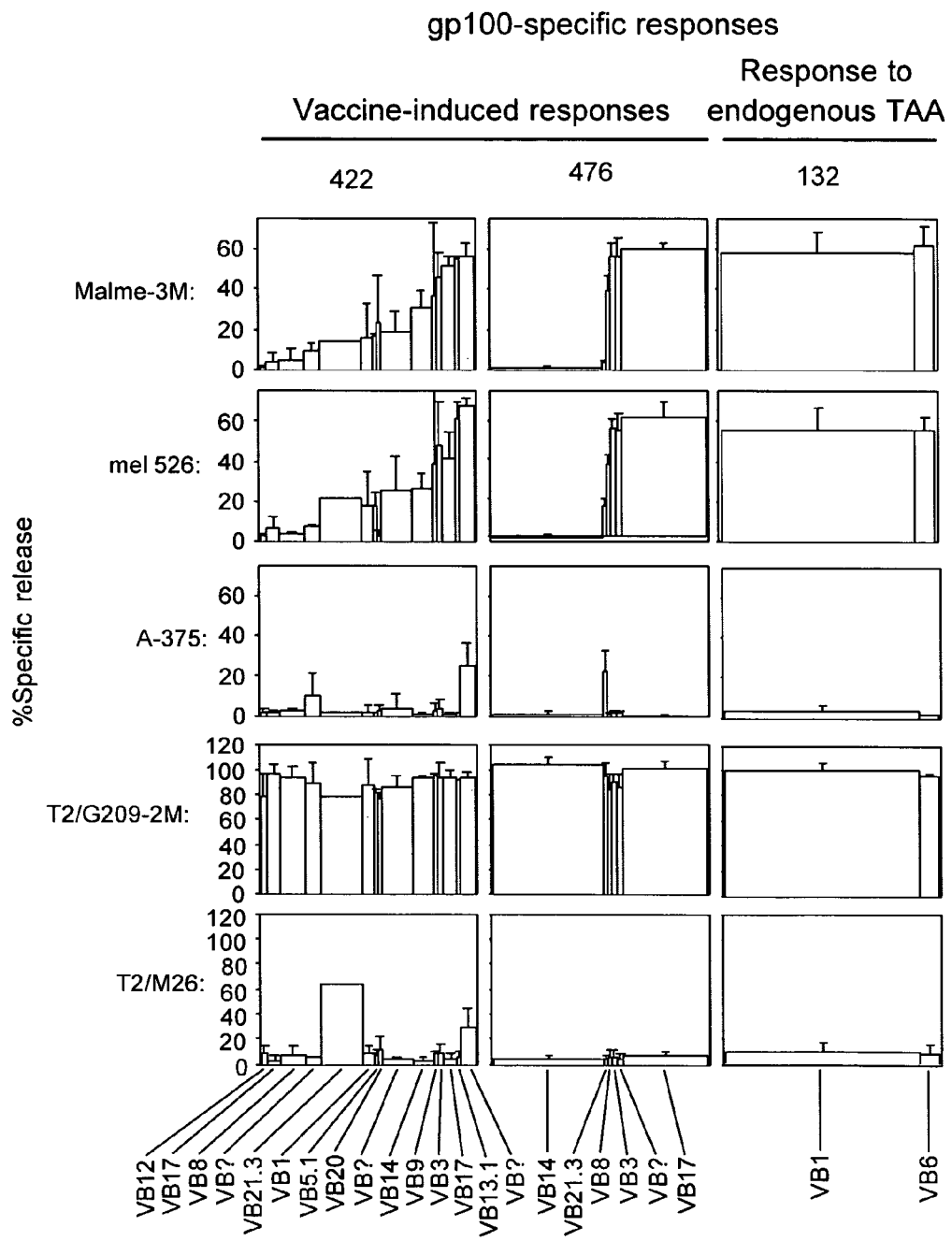

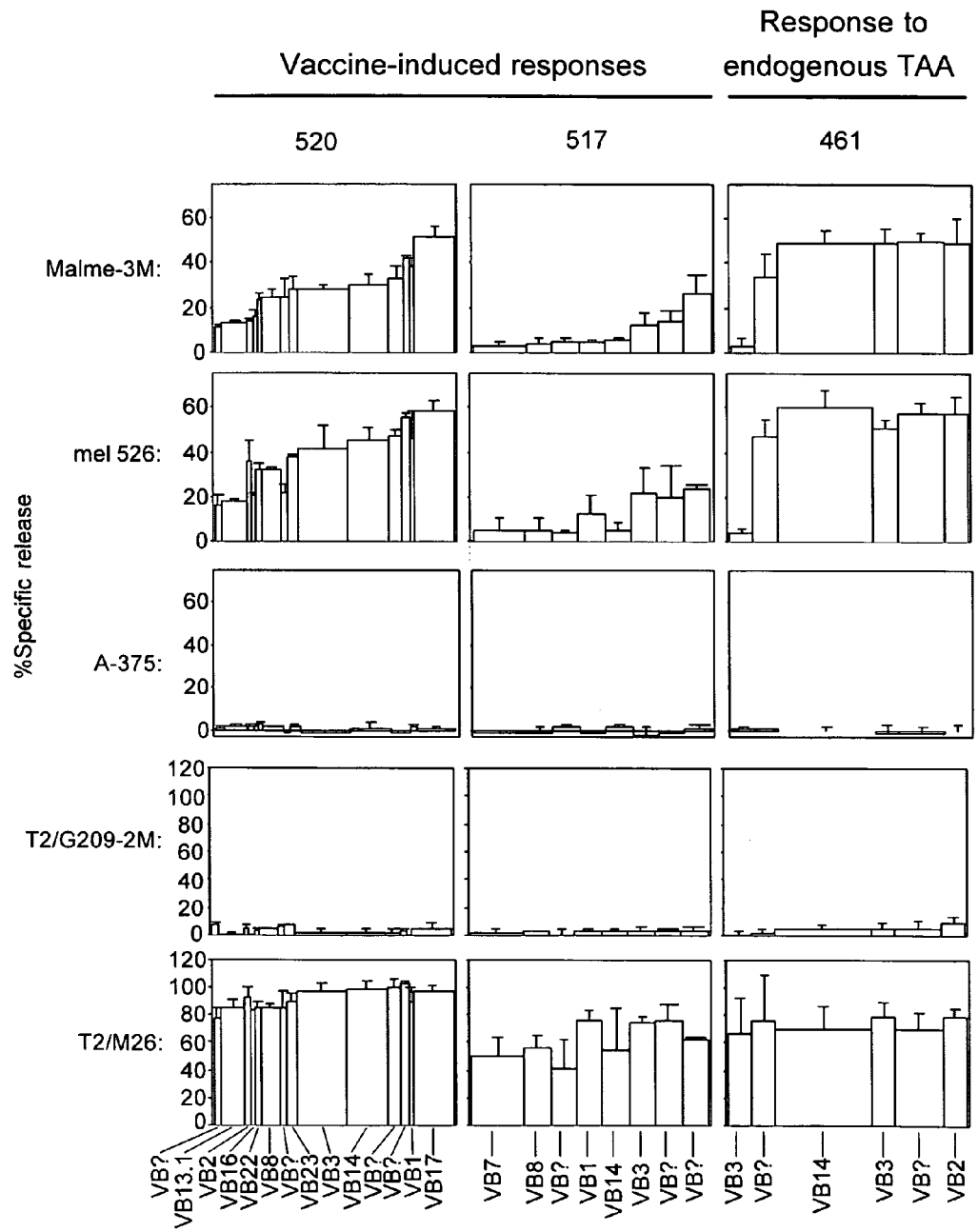

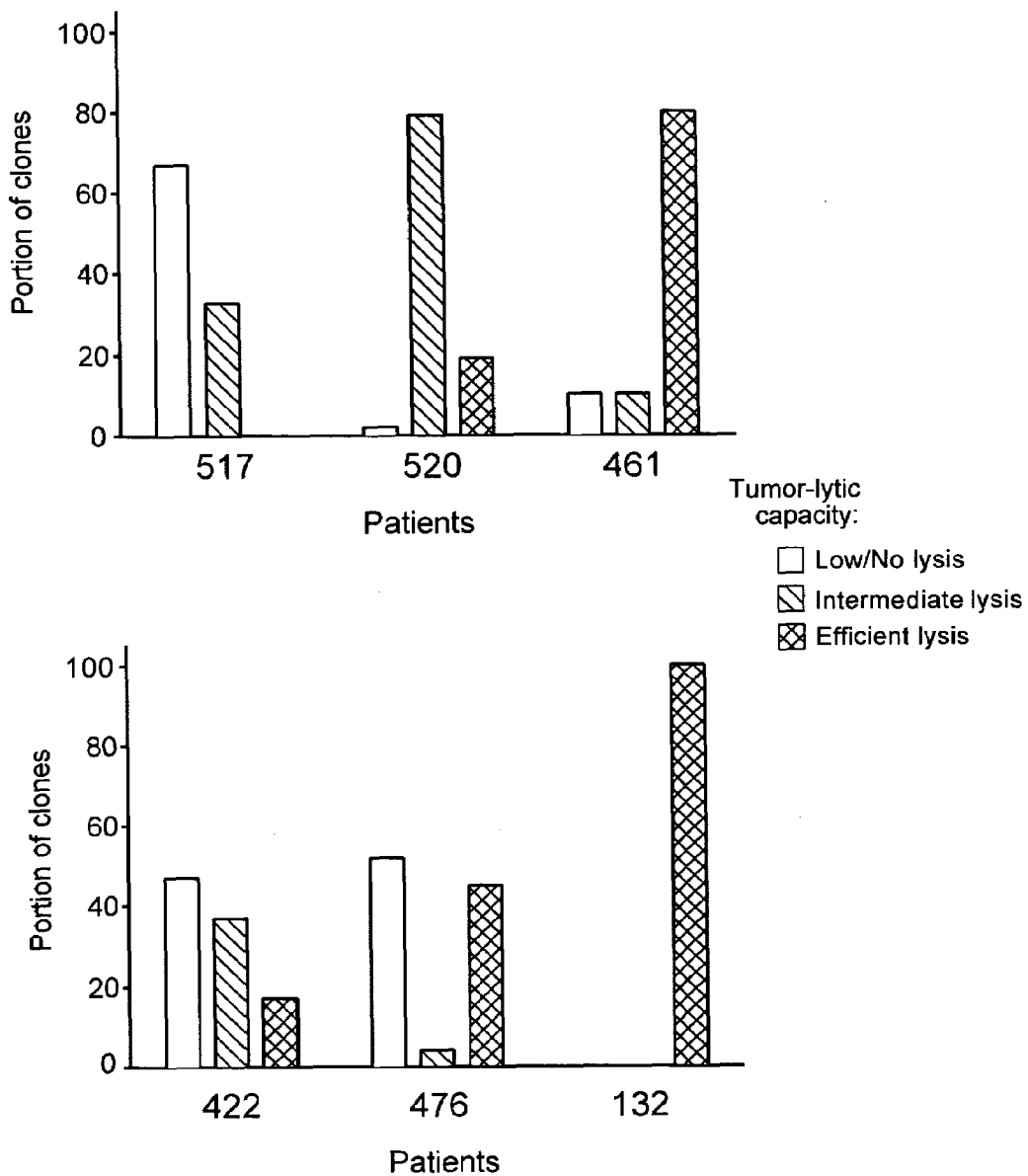

G209n (Native) peptide

G209-2M (Heteroclitic) peptide

MART-specific clones

Gp100-specific clones

MART-specific clones gp100-specific clones

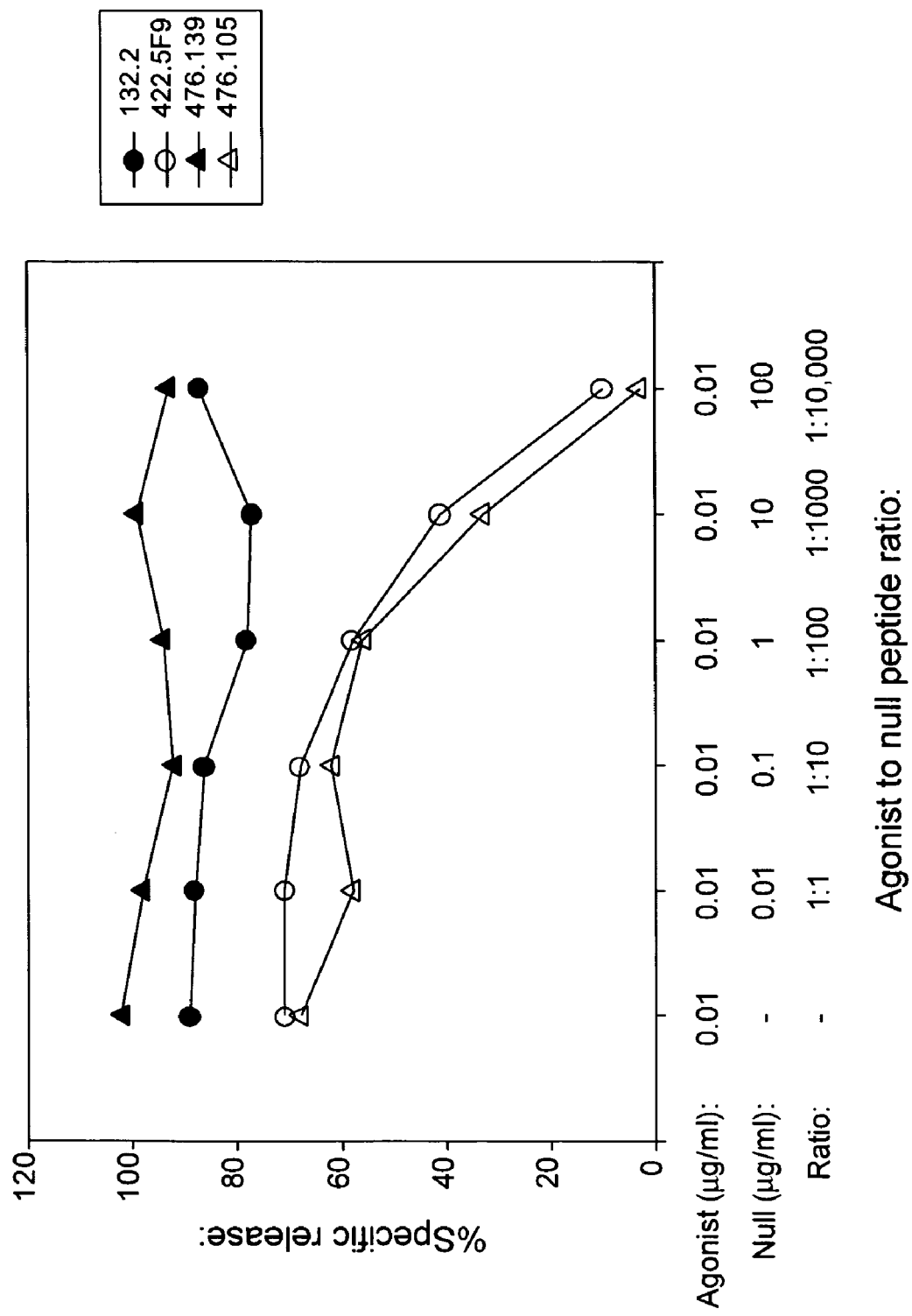

METHODS FOR PRODUCING TARGET CELL REACTIVE LYMPHOCYTES

CROSS-REFERENCE TO RELATED APPLICATIONS

Pursuant to 35 U.S.C. § 119 (e), this application claims priority to the filing date of the U.S. Provisional Patent Application Ser. No. 60/591,889 filed Jul. 27, 2004; the disclosure of which is herein incorporated by reference.

GOVERNMENT RIGHTS

This invention was made with government support under federal grant no. NIH R01 CA 090809 awarded by the NIH. The United States Government may have certain rights in this invention.

INTRODUCTION

1. Background of the Invention

Interest in the development of peptide-vaccination strategies for cancer have driven driven by the possibility of inducing tumor associated antigen (TAA) specific T cell responses that can efficiently eliminate a patients' cancer cells. The anti-tumor potential of TAA-specific CD8+ T cells has been illustrated by the demonstrated capacity of adoptive T cell therapy to reduce tumor size. While endogenous anti-tumor CD8+ T cell responses may already exist in some cancer patients, vaccination with TAA-derived peptides, and in particular heteroclitic peptide analogs, increases the frequency of TAA-specific T cells to detectable levels in many patients. However, the presence of TAA-specific T cells elicited by vaccination often does not correlate with clinical responses.

There are a large number of strategies to increase the magnitude of T cell responses to peptide vaccines. These include various adjuvants such as IFA, IL-12, GM-CSF, anti-CTLA-4 antibodies, and heat shock proteins. Thus far, none of these approaches have improved clinical responses.

As such, there is a continued need for the development of improved vaccination strategies.

2. Relevant Literature

Bullock et al., J. Immunol. (2003) 170: 1822-1829; Oh et al., J. Immunol. (2003) 170: 2523-2530 and Xu et al., (2003) J. Immunol. 171: 2251-2261.

SUMMARY OF THE INVENTION

Methods and compositions are provided for the induction of target cell reactive T-lymphocytes, including cytolytic T-lymphocytes. In practicing the subject methods, a lymphocyte population is contacted with an effective amount of a mixture of peptide antigens associated with the target cell of interest, where the mixture comprises peptides that are both active and inactive in the generation of reactive lymphocytes. Also provided are compositions, kits, and systems for practicing the subject methods. The subject invention finds use in a variety of different applications, including therapeutic applications.

BRIEF DESCRIPTION OF THE FIGURES

FIG. 1B, the estimated percentage of total CD8+ cells that are also tetramer+/CD8+ for each patient are: 422: 2.5%; 476: 0.31%; 132: 0.22%; 517: 0.23%; 520: 0.12%, 461: 0.50%. b. Micro-cytotoxicity $^{51}$Cr-release assay with tetramer+/CD8+ cells isolated by FACS from the PBMC from patient 422. Isolated cells were assayed for lysis of T2 cells treated with relevant (G209-2M, G209n) or irrelevant (CMV) peptide, or mel 526 melanoma cells. Sorted cells were combined with 250 target cells at 13:1 E:T ratios for 4 hours and supernatants were assayed for percent specific release of radio-label.

FIGS. 2A-2C. Endogenous cytolytic T cells are more efficient than vaccine-elicited cytolytic T cells in lysing melanoma cells. Cells from 84 clonal CTL lines were assayed for lysis of melanoma cells mel 526, Malme-3M and A-375 in $^{51}$Cr-release cytotoxicity assays. Mel 526 and Malme-3M are HLA-A2.1+ and express both gp100 and MART-1. A-375 cells are HLA-A2.1+ but do not express either gp100 or MART-1 and served as a negative control. T2 cells treated with 1 µg/ml G209-2M or M26 peptides served as controls for antigen-specific lysis. The CTL clones assayed were selected to represent tetramer+ subsets expressing different T cell receptor V-beta subunits. Dominating tetramer+ populations in each patient were represented with two or more clones. Each CTL clone was assayed in triplicate wells and the data displayed are averages of two independent experiments. CTL clones from the same patient expressing similar V-beta subunits which exhibited different lysis potential were viewed as separate subsets. Each assay was performed at 10:1 effector to target ratio as detailed in the methods section. FIGS. 2a-2b. Efficiency in melanoma cell lysis as a function of relative population size. The height of each bar represents % specific lysis, while the width represents the relative size of the tetramer+ subpopulations (defined by V-beta expression) in each patient. Population size was defined as the percent of CTL clones from each patient expressing the same V-beta. Error bars show standard deviation (SD) between two experiments with each clone and/or between different clones where more than one clone was analyzed. FIG. 2C. CTL clones derived from each patient were classified as "efficient" (>40%), "intermediate" (>10%, <40%) or "poor/no lysis" (<10%) in lysis of melanoma cells. Each bar represents the portion of total clones from each patient with "efficient", "intermediate" or "poor/no" melanoma lysis potential.

FIGS. 4A-4B. Target cells pulsed with a combination of agonist and "null" peptides are selectively lysed by high RE but not low RE T cells. High (132.2 and 476.139) and low (422.5F9 and 476.105) RE CTL clones were assayed for lysis of T2 cells pulsed with a. 10 ng/ml native G209n peptide (ITDQVPSFV (SEQ ID NO:1); agonist) and various concentrations of G209-3A peptide (ITAQVPSFV (SEQ ID NO:2); null) at ratios of agonist:null peptide ranging from 1:1 to 1:10,000, or b. with a constant ratio agonist:null peptides of 1:10,000 at total peptide concentrations ranging from 100 ng/ml to 100 µg/ml. Lysis of T2 cells pulsed with agonist only is shown for comparison.

DETAILED DESCRIPTION OF THE INVENTION

Figure 1A:
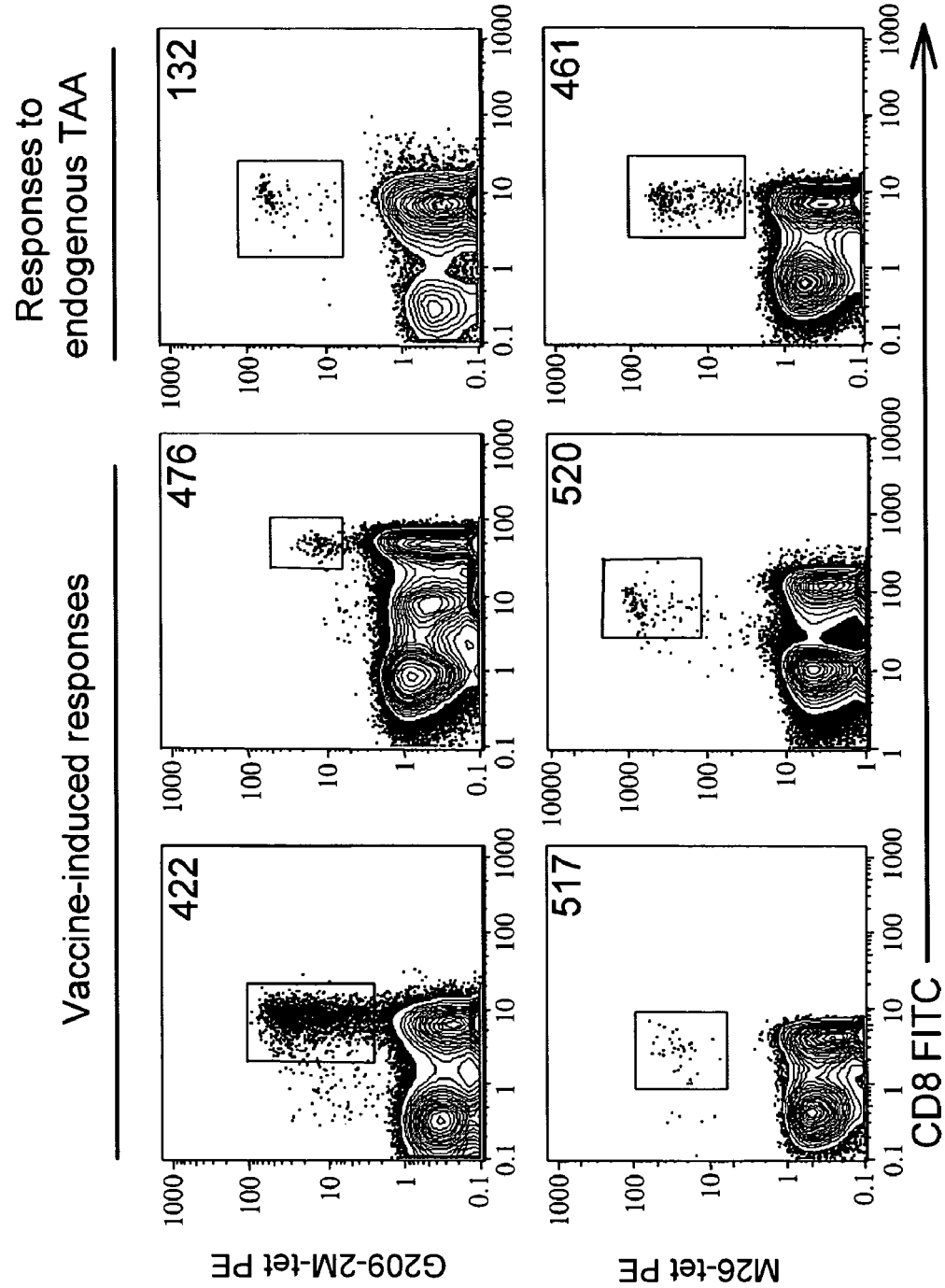
FIGS. 1A-1B. Melanoma patient samples selected for analysis of RE for melanoma cells. a. Six patients with T cell responses specific for MART-1 or gp100 were selected for analysis. PBMC from each patient were stained with PE-conjugated peptide-MHC tetramers: G209-2M-tet PE or M26-tet PE, and co-stained with anti-CD8 FITC and anti-CD14, -CD19, and -CD4 Cy5PE. The plots shown are gated for CD14-, CD19-, and CD4-cells. Tetramer+/CD8+ cells are boxed.

Methods and compositions for producing target cell reactive lymphocytes, e.g., cytolytic T-lymphocytes, in a subject are provided. In practicing the subject methods, a lymphocyte population is contacted with an effective amount of a target cell peptide mixture of active and inactive peptides to produce lymphocytes reactive for the target cell. Also provided are compositions, kits, and systems for practicing the subject methods. The subject invention finds use in a variety of different applications, including therapeutic applications.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the subject invention, the methods will be described first, followed by a review of representative applications in which the methods find use, as well as a review of representative kits and systems thereof that find use in practicing the subject methods.

Methods

As summarized above, the subject invention provides methods of producing target specific reactive lymphocytes, including target specific cytolytic T-cells, from an initial population of lymphocytes, e.g., a naïve or unstimulated T-cell population. In other words, the invention provides methods of making lymphocytes reactive for a specific target from a parent population of lymphocytic cells. By reactive for a specific target is meant that the cell is cytolytic for the target, or mediates destruction of the target cell by some means, e.g., by secreting cytokines to activate other T cells, or causing target cells to undergo apoptosis (suicide) via other cytokines or mediators (e.g., Fas). By "cytolytic lymphocyte" is meant a non-B lymphocyte that exhibits cytolytic activity, where cytolytic lymphocytes include, but are not limited to: cytolytic T-cells, natural killer (NK) cells, NKT cells and CD4+ T cells, which cells may degranulate and kill target cells. While in the broadest sense the invention is directed to the production of reactive lymphocytes as defined above, in many embodiments the methods and compositions of the invention are employed for the production of cytolytic T-cells, usually CD8+ T cells. Accordingly, for ease of further description of the invention, the invention will now be further described in terms of methods and compositions for use in the production of cytolytic T-cells. However, the invention is not limited to the production of cytolytic T-cells, but includes the production of non-T-cell reactive lymphocytes, and helper T cells, as described above.

By "cytolytic T-cell" is meant a cell that is cytotoxic for a target cell, i.e., a cell that is specifically reactive with, and capable of killing, a target cell, where the target cell may be any undesired cell, e.g. a neoplastic cell; an autoreactive cell such a memory B cell, autoreactive T cell, etc.; a cell chronically infected with a virus or other intracellular pathogen; and the like.

A feature of the cytolytic cells produced by the subject methods in certain embodiments is that the cells have a high Recognition Efficiency (RE) for the target cells for which they are cytolytic. By high Recognition Efficiency is meant that the recognition efficiency or RE of the cytolytic lymphocytic cells produced by the subject methods, as determined by the protocol described in the experimental section, infra, is at least about $10^{-9}$ to $10^{-12}$ M. A further feature of certain embodiments of the subject methods is that when a plurality or population of cytolytic lymphocytes are generated from a parent population of lymphocytes, the generated population of cytolytic lymphocytes is more homogenous with respect to the RE values of its member cells as compared to a population of lymphocytes generated using a homogenous peptide activator agent. In certain embodiments, the standard deviation with respect to the RE values of the members of the population produced by methods of the subject invention does not exceed about one log from the RE range of representative embodiments that provides for efficient target reactivity (e.g., at least about $10^{-9}$ to $10^{-12}$ M).

In practicing the subject methods, a parent population of lymphocytes, e.g., T-cells, is contacted with a target cell specific peptide mixture to produce the desired population of target cell cytolytic lymphocytes. The initial or parent T-cell population may be a naive population, or a population that has been pre-treated with another activator, e.g., a heteroclitic peptide composition, so as to be a mixed RE population of both high and low RE cells. As described in greater detail below, the contacting may occur in vitro or in vivo, depending on the particular application in which the methods are employed.

By target cell specific peptide mixture is meant a mixture or combination of two or more different peptides, where the mixture includes at least a first peptide that is an active peptide, e.g., an agonist, and at least a second peptide that is inactive, e.g., a null or antagonist peptide. For purposes of the present invention any two given peptides are considered to be different or distinct if their sequences differ from each other, when aligned for maximum agreement, by at least one residue or amino acid. While a given target cell specific peptide mixture may include only two different or distinct peptides, i.e., the active and inactive peptides as described above, in certain embodiments the target cell specific peptide mixture may include three or more different peptides, where the total number of different or distinct peptides in a given mixture may be as a great as about 10 or greater, e.g., as great as about 25 or greater, where the total number of different peptides in a given mixture may not, in certain embodiments, exceed about 50.

As indicated above, the peptide mixtures employed in the subject methods include both active and inactive peptides. In many embodiments, active peptides employed in the subject methods are peptides that are derived from proteins that distinguish or differentiate the target cell from other cells that can be present in the environment or vicinity of the target cell when it is to be contacted with the cytolytic lymphocyte produced by the present methods. For example, where the target cell is a tumor cell, the active peptides of the peptide mixture may be peptides derived from a tumor associated antigen (TAA) of the target tumor cell. Where the target cell is an autoreactive lymphocyte, the peptides may include antibodies present on the surface of B cells, T cell antigen receptors present on the surface of T cells; and the like. Where the target cell is a chronically infected cell, the peptides may be pathogen proteins, e.g. viral antigens, etc. Specific representative examples of TAAs are provided in the Experimental Section below.

As is known in the art, active peptides are agonist peptides that, when presented by a target cell to a cytolytic T-cell specific for the protein from which the peptide is derived, cause the T-cell to bind and lyse (react to) the target cell. Active peptides may range in size, and in many representative embodiments range from about 8 to about 16 residues in length, such as from about 8 to about 16 residues in length, including from about 6 to about 40 residues in length. Active peptides may include immunodominant epitopes of the protein. The active peptides may include a sequence that is found in the sequence of the target protein, e.g., TAA, or a sequence that is substantially identical to a sequence found in the sequence of target protein. By substantially identical is meant a sequence that has at least about 85%, such as at least about 90%, including at least about 95% sequence identity with a sequence of the target protein, where sequence identity is measured by the BLAST compare two sequences program available on the NCBI website using default settings, as measured over the entire length of the protein, where the website has the address made up by placing "www." in front of and ".gov" in back of "ncbi.nlm.nih".

A given peptide mixture employed in a method according to the subject invention may include a single active peptide, or two or more different active peptides, where the number of different active peptides in a given mixture may be as high as 10 or higher, but in representative embodiments does not exceed about 50.

As indicated above, the peptide mixtures of the present invention also include inactive peptides. The term inactive peptide is used to describe peptides that are either null peptides or antagonist peptides. As is known in the art, null peptides are peptides that, when presented by a target cell to a cytolytic T-cell specific for the corresponding antigen, do not elicit a cytolytic response with respect to the target cell, such that the cytolytic T-cell does not kill the target cell. Also as is known in the art, antagonist peptides are peptides that inhibit a cytolytic T-cell from lysing a target cell.

Inactive peptides may range in size, and in many representative embodiments range from about 8 to about 16 residues in length, such as from about 8 to about 16 residues in length, including from about 6 to about 40 residues in length. The inactive peptides may or may not include a sequence that is found in the sequence of the target protein, e.g., TAA, or a sequence that is substantially identical to a sequence found in the sequence of target protein. By substantially identical is meant a sequence that has at least about 85%, such as at least about 90%, including at least about 95% sequence identity with a sequence of the target protein, where sequence identity is measured as described above. As such, in certain embodiments the inactive peptides may have sequences that are completely different from any sequence found in the target antigen, while in other embodiments the inactive peptides may include a sequence that is the same as or substantially identical to a sequence found in the target antigen, e.g., the tumor associate antigen of the target cell. Furthermore, in certain embodiments the inactive peptides may have sequence similarity to the active peptides, as described above.

A given peptide mixture employed in a method according to the subject invention may include a single inactive peptide, or two or more different inactive peptides, where the number of different inactive peptides in a given mixture may be as high as 10 or higher, but in representative embodiments does not exceed about 50.

The ratio of active to inactive peptides in a given target cell specific mixture employed in the subject methods is chosen to provide for the desired production of high RE cytolytic T-cells. In representative embodiments, the ratio of active to inactive peptides in a given mixture ranging from about 1:100 to about 1:100,000, such as from about 1:100 to about 1:100,000, including from about 1:1 to about 1:10,000,000 (or the inverse ratio).

As indicated above, in practicing the subject methods an initial T-cell population is contacted with a target cell specific peptide mixture in a manner sufficient to produce a desired cytolytic T-cell population having a high RE for the target cell. The conditions under which contact occurs may be in vitro or in vivo.

For in vitro applications, a T-cell population and target cell specific peptide mixture are combined and incubated, e.g., in an aqueous media that includes one or more needed or desired factors, and maintained under conditions suitable for desired production of the product T-cell population to occur. Representative mediums that may be employed include but are not limited to: currently employed culture mediums, which mediums may be liquid or semi-solid, e.g., containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin. The amounts of reagents employed during this step may vary and are readily determined by those of skill in the art, where representative parameters are provided in the Experimental Section, below. Following contact, the product composition is maintained, typically at a temperature ranging from about 36° C. to about 38° C., including from about 25° C. to about 42° C., for a period of time ranging from about 1 hour to about 8 hours, including from about 0.5 hour to about 24 hours.

For in vivo applications, an effective amount of a peptide mixture is administered to a subject, e.g., patient, to produce the desired target cell specific cytolytic T-cells in the subject. The peptide mixture may be administered by any suitable means, including but not limited to: parenteral, subcutaneous, intraperitoneal, intrapulmonary, and intranasal. Representative Parenteral infusions include, but are not limited to: intramuscular, intravenous, intraarterial, intraperitoneal, or subcutaneous administrations. In addition, the peptide composition may be suitably administered by pulse infusion, including with declining doses of the peptide composition. As desired, dosing may be given by injections, such as intravenous or subcutaneous injections, depending in part on whether the administration is for a short or long period of time.

For the prevention or treatment of disease, the appropriate dosage of peptide composition will depend on the type of disease to be treated, the severity and course of the disease, whether the peptide composition is administered for preventive or therapeutic purposes, previous therapy, a given patient's clinical history and response to the peptide composition, and the discretion of the attending health care professional. The peptide composition is suitably administered to the patient at one time or over a series of treatments.

Depending on the type and severity of the disease, about 1 mg/kg to 15 mg/kg (e.g., 0.1-20 mg/kg) of peptide composition is an initial candidate dosage for administration to the patient, whether, for example, by one or more separate administrations, or by continuous infusion. A typical daily dosage might range from about 1 mg/kg to 100 mg/kg or more, depending on the factors mentioned above. For repeated administrations over several days or longer, depending on the condition, the treatment may be sustained until a desired suppression of disease symptoms occurs. However, other dosage regimens may be useful. The progress of this therapy is easily monitored by conventional techniques and assays.

The peptide composition may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the peptide composition to be administered will be governed by such considerations, and is the minimum amount necessary to prevent, ameliorate, or treat a disease or disorder. The peptide composition need not be, but may optionally be formulated with one or more agents currently used to prevent or treat the disorder in question. The effective amount of such other agents depends on the amount of peptide mixture present in the formulation, the type of disorder or treatment, and other factors discussed above. These are generally used in the same dosages and with administration routes as used hereinbefore or about from 1 to 99% of the heretofore employed dosages.

Practice of the subject methods results in the production of cytolytic T-cells as described above. Specific representative cytolytic T-cells of interest that may be prepared by the subject methods include, but are not limited to: T-cells that are cytolytic, i.e., capable of killing or cytotoxic for, a wide variety of different types of target cells, such as disease causing cells, e.g., hazardous/pathogenic cellular microorganisms, such as *Pneumococcus, Staphylococcus, Bacillus, Streptococcus, Meningococcus, Gonococcus, Eschericia, Klebsiella, Proteus, Pseudomonas, Salmonella, Shigella, Hemophilus, Yersinia, Listeria, Corynebacterium, Vibrio, Clostridia, Chlamydia, Mycobacterium, Helicobacter* and *Treponema*; protozoan pathogens, and the like; where intracellular pathogens are of particular interest, as well as disease causing cells endogenous to the host, e.g., autoreactive cells, neoplastic cells, including cancerous cells, and the like. Specific representative neoplastic target cells include those found in the following representative types of cancers: melanomas, carcinomas, such as squamous cell carcinomas, adenocarcinomas, transitional cell carcinomas, basal cell carcinomas, etc., which may include colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma, lymphomas and leukemias, gliomas, astrocytomas, sarcomas, etc.

The subject methods find use in a variety of different applications, where representative applications are reviewed in greater detail below.

Utility

The subject methods find use in a variety of different applications where one wishes to produce reactive lymphocytes, e.g., cytolytic T-cells. One representative application in which the subject methods find use is in therapeutic protocols to produce therapeutic agents, e.g., therapeutic cytolytic T-cells. In such applications, the methods are employed to produce a cytolytic T-cell population that is specific for a target cell type that is responsible for a disease condition afflicting a subject or patient. As convenient, the cytolytic T-cell population may be produced in vitro and then administered to a host, or produced directly in the host, such that the peptide mixture is administered to the host as a vaccine.

In those in vitro embodiments, the product population may be further processed or screened to identify and isolate those cells of the product population that have desirable cytolytic properties. For example, the methods described in U.S. application Ser. No. 60/530,798 (the disclosure of which is herein incorporated by reference) may be employed to screen and isolate cytolytic cells from the product population of in vitro embodiments of the subject methods. Briefly, in the isolation methods described in the Ser. No. 60/530,798 application, a sample is contacted with a target cell stimulator, e.g., a neoplastic cell, and a detectably labeled granule membrane protein specific binding agent. Following contact, any resultant labeled lymphocytes, e.g., T-cells, are identified as lymphocytes cytolytic for the target cell. The resultant enriched isolated T-cell composition may then be expanded ex vivo to produce an increased population of cytolytic T-cells. In certain embodiments, a feature of the subject methods is that the harvested population of cells is expanded, where the expansion step occurs at some point in time prior to reintroduction of the cells to the subject of origin. In the expansion step, the number of T-cells in the harvested cell collection is increased, e.g., by at least about 4 fold, such as by at least about 4 fold as compared to the originally isolated amount, such that at least in certain embodiments the final number may be from about 100- to about 100,000-fold or more greater than the original number of cells. As such, the isolated cells are proliferated to produce an expanded population of harvested T-cells.

The isolated cells may be proliferated in this step according to any convenient protocol. For example, the cells are proliferated or enhanced by contacting the cells with an expansion agent, by which is meant an agent that increases the number of cells by causing cellular proliferation. A variety of different such agents are known, where representative agents include, but are not limited to: growth factors, accessory cells, ligands of specific activation receptors that may be monoclonal antibodies or antigens, and the like. One representative such protocol is described in U.S. Pat. No. 6,352,694; the disclosure of which is herein incorporated by reference.

Depending on the particular embodiment being practiced, an effective amount of the peptide mixture or in vitro cytolytic T-cells produced thereby is administered to the host. By effective amount is meant an amount effective to achieve the desired treatment of the host. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

In certain embodiments, the subject/host/patient being treated may have been pretreated with an initial vaccine, e.g., comprising heteroclitic peptides, in order to initially stimulate or activate a naive cytolytic T-cell population.

A variety of hosts are treatable according to the subject methods. In certain embodiments, such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Pharmaceutical Formulations

Therapeutic formulations of the peptide mixtures of the subject invention are also provided. As desired, the peptide mixtures may be prepared for storage by mixing the peptide mixtures having the desired degree of purity with optional physiologically acceptable-carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, such as those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration are generally sterile, where sterility may readily be accomplished by filtration through sterile filtration membranes.

Sustained-release preparations may be prepared. Suitable examples of sustained-release preparations include semipermeable matrices of solid hydrophobic polymers containing the polypeptide variant, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Kits & Systems

Also provided are kits and systems that find use in practicing the subject methods, as described above. For example, kits and systems for practicing the subject methods may include one or more pharmaceutical formulations, which include one or both of the peptide components of the above-described peptide compositions or mixture, i.e., the inactive and active peptide components. As such, in certain embodiments the kits may include a single pharmaceutical composition, present as one or more unit dosages, where the composition includes both the active and inactive peptides of the above described mixtures. In yet other embodiments, the kits may include two or more separate pharmaceutical compositions, each containing either an active or inactive peptide component.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The term "system" as employed herein refers to a collection of active and inactive peptide components, present in a single or disparate composition, that are brought together for the purpose of practicing the subject methods. For example, separately obtained active and inactive peptides brought together and coadministered to a subject, according to the present invention, are a system according to the present invention.

The following examples are offered by way of illustration and not by way of limitation.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

I. Methods

A. Patient samples. Peripheral blood mononuclear cell (PBMC) samples were isolated from melanoma patients after vaccination with the heteroclitic peptides MART 26-35 (27L) (ELAGIGILTV (SEQ ID NO:3)) and gp100 209-217 (210M) (IMDQVPSFV (SEQ ID NO:4)) in incomplete Freund's adjuvant (IFA) at the USC Norris Cancer Center, Los Angeles, Calif. under an IRB approved protocol. PBMC samples were stored at −130° C. and were thawed the day before an experiment for overnight culture in CTL media. The following morning, viable cells were isolated by ficoll density centrifugation, washed, and resuspended to the appropriate concentration in 90% Iscove's Modified Dulbecco's medium (IMDM), 10% fetal bovine serum (FBS).

B. Flow Cytometry Analysis. For detection/isolation of peptide-specific T cells, patient PBMC samples were stained and analyzed by FACS as previously described Lee et al., Nat. Med. (1999) 5: 677-685. Briefly, cells were stained with anti-human CD8– fluorescein isothiocyanate (FITC) (Caltag) and CD19-CyChrome (BD Biosciences) antibodies (Ab), and HLA-A*0201/peptide tetramer-phycoerythrin (PE). The final staining dilution of each Ab was 1/200 and 1/80, respectively. Tetramer-PE was titrated for optimal staining, usually between 1 and 10 µg/ml. For TCR Vbeta-typing, cells were divided in 7 aliquots and stained with CD8 PerCP-Cy5.5 (BD Biosciences), tetramer-PE, and a panel of 2 or 3 different anti-Vbeta mAb labeled with FITC, allophycocyanin (APC), or both. Cells were incubated at room-temperature for 30 mins, washed, then analyzed using a two-laser, 4-color FACSCalibur (Becton Dickinson, San Jose, Calif.), or sorted using a FACSVantage flow cytometer (Becton Dickinson, San Jose, Calif.). Lymphocytes were identified by forward and side scatter signals, then selected for CD8+ and tetramer+. Up to one million events were acquired and analyzed using FlowJo (TreeStar, San Carlos, Calif.).

C. Generation of CTL clones. CD8+ T cell clones were obtained by FACSorting individual tetramer+ cells from PBMC samples prepared for flow cytometry as described above. CD8+ tetramer+ T cells were sorted at one cell per well into 96 well plates containing 100 µl of CTL media (IMDM, with 10% FBS, 2% human AB sera, and Penicillin, Streptomycin, and L-Glutamine, supplemented with 100 U/ml IL-2) under sterile conditions using a FACSVantage (Becton Dickinson, San Jose, Calif.). Sorted cells were expanded in vitro using standard protocols. Briefly, irradiated feeder cells (JY cells and fresh PBMCs) were added to wells containing the sorted T cells and the 96 well plates were incubated at 37° C., 7% $CO_2$ to allow for growth. Potential clones become visible around day 14 and were then transferred to 24 well plates containing 1 ml CTL media with 100 U/ml IL-2. Wells were selected based on cell confluency for expansion and further analysis. Clones confirmed to be tetramer+ were expanded in T-25 flasks containing irradiated JY cells and fresh PBMCs in 25 ml CTL media containing PHA. IL-2 was added to a final concentration of 50 U/ml on day 1 and then every 2 days thereafter for 2 weeks.

D. Cytotoxic Assays. 1. Target Cells: The HLA-A*0201+ melanoma lines Malme-3M and A375 were purchased from ATCC and maintained according to their instructions. The HLA-A*0201+ melanoma line mel526 was a kind gift from Dr. Y. Kawakami. While Malme-3M and mel526 express both MART and gp100, A375 does not express MART or gp100 and served as a negative control. Expression (or lack of) of these antigens by each cell line was further confirmed by immunohistochemical staining. These cells adhere to plastic and were trypsinized using Trypsin/EDTA solution (Gibco) before use. They were washed and resuspended to the appropriate concentration (usually $10^5$/ml) in 90% IMDM, 10% FBS.

2. Determination of recognition efficiency (RE): $^{51}$Chromium ($^{51}$Cr)-labeled T2 targets were pulsed with a range of peptide concentrations, generally starting at $10^{-7}$ M and decreasing by log steps to $10^{-13}$ M. T cell clones were incubated with T2 targets at 10:1 E:T ratios for 4 hours, then $^{51}$Cr release was measured and percentage cytotoxicity calculated by standard methods. Prior to each cytotoxicity assay, clones underwent ficoll-hypaque centrifugation to remove dead feeder cells, and were determined to be >80% CD8+ tetramer+ T cells by FACS. The E:T ratio was based upon live T and target cells. For each T cell clone, % cytotoxicity was plotted against peptide concentration. The peptide concentration at which the curve crosses 40% cytotoxicity was defined as the RE of that clone (Marguiles, Nat. Immunol. (2001) 2:669-670.

3. Microcytotoxic assay: Cells were isolated directly from PBMC from patient 422 by FACS as described above. Cells were collected in microfuge tubes containing 1 ml ice cold 90% IMDM, with 10% FBS. Collected cells were washed and resuspended to 83,300 cells/ml in 90% IMDM, with 10% FBS. Targets were prepared as described above and resuspended to 8,300 cells/ml in 90% IMDM, with 10% FBS. 2,500 sorted cells (30 µl) and 250 target cells (30 µl) were transferred to a microcentrifuge tube (VWR), centrifuged 1 min at 200×g and incubated 4 hours at 37° C. Percent specific release of $^{51}$Cr was calculated from 40 µl cell-free supernatant.

II. Results

A. T cell responses to tumor-associated antigens (TAAs) in melanoma patients. To address the complexity of T cell responses against melanoma in vivo, patients with vaccine-induced or endogenous tumor antigen-specific responses were selected. In recent cancer vaccine trials, many melanoma patients who received heteroclitic peptide vaccines gp100 $_{209-217\,(210M)}$ (IMDQVPSFV (SEQ ID NO:4); G209-2M) and MART-1 $_{26-35\,(27L)}$ (ELAGIGILTV (SEQ ID NO:3); M26) had measurable CD8+ peptide-specific T cell responses in PBMC detected by peptide-MHC (pMHC) tetramer staining. In addition, TAA-specific T cell responses could be detected in some patients without vaccination, suggesting the existence of an endogenous anti-tumor T cell response in these patients.

For the current study, we selected samples from six melanoma patients from these trials—four with vaccine-elicited responses (samples 422, 476, 517, and 520) and two with endogenous T cell responses (132 and 461)—for detailed analyses of TCR V-beta usage, RE for the target peptide, and tumor cytotoxicity. These six patient samples had peptide-specific T cell populations detectable with G209-2M-tetramers (patients 422, 476 and 132) or M26-tetramers (patients 517, 520 and 461) ranging from 0.1 to 2.5% of total CD8+ T cells (FIG. 1a).

Figure 1B:
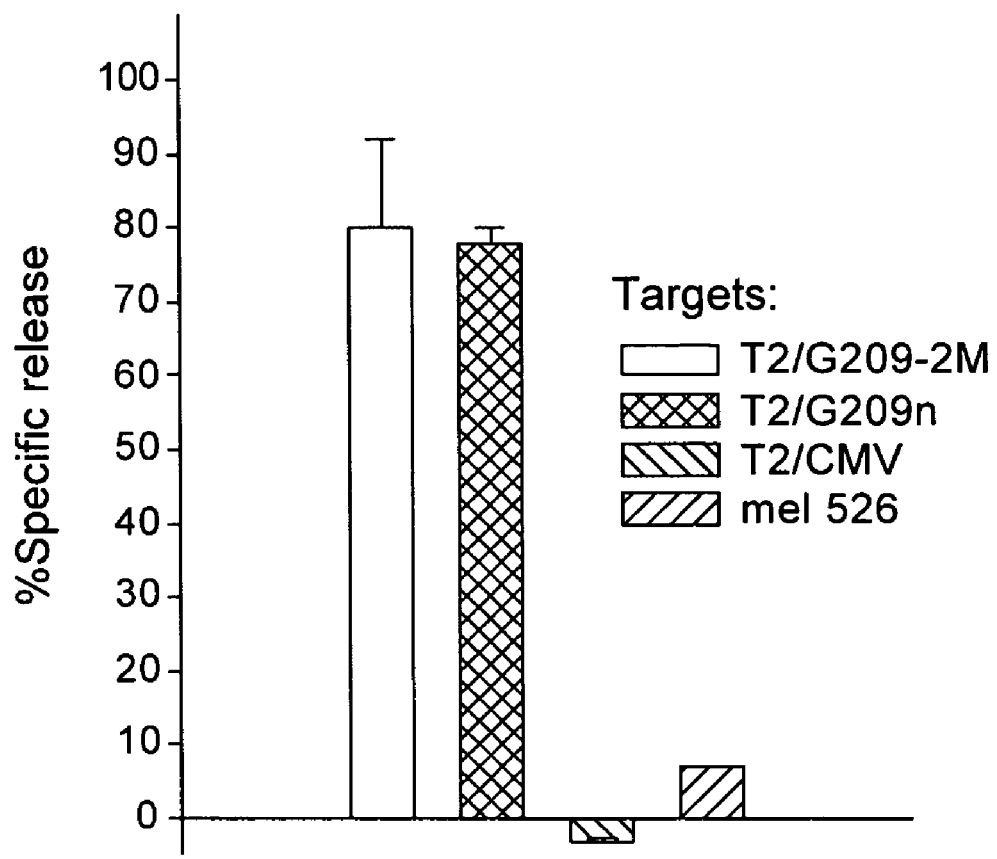

B. Vaccine-elicited T cells are cytolytic directly ex vivo. Patient 422 had the largest detectable TAA-specific CD8+ T cell response (2.5% G209-2M tetramer+), and thus sufficient numbers for examination of lytic function immediately following isolation. To test whether peptide vaccine-induced T cell responses were functionally active directly ex vivo, T cells isolated by tetramer-guided cell sorting from patient 422 were tested for lysis of peptide-pulsed and melanoma target cells in micro-cytotoxic assays (FIG. 1b). The directly isolated tetramer+ T cells from this patient specifically lysed T2 cells pulsed with high concentrations (1 µg/ml) of G209-2M- and native (G209n) peptides, but not with M26-pulsed or melanoma targets. This result shows that while a significant portion of the vaccine-elicited T cells from patient 422 may be function in vivo, they did not have significant tumor lysis activity.

C. Vaccine-elicited T cells have varied capacity to lyse melanoma targets. We reasoned that analysis of a set of clonal CTL lines that represented the tetramer+ population would provide an accurate estimate of the complexity of the TAA-specific T cell response in each patient. A large number of clonal CTL lines (>200) were generated by fluorescence activated cell sorting (FACS) of individual tetramer+ cells directly from PBMC samples (Table 1).

TABLE 1

CTL clones established from each patient represent a random selection from the tetramer-reactive CD8+ parent population.

| TCR VB family | [a]Patient 422 [b]CTL clones | Patient 422 [c]Tet+ PBMC | Patient 476 CTL clones | Patient 476 Tet+ PBMC | Patient 132 CTL clones | Patient 132 Tet+ PBMC | Patient 461 CTL clones | Patient 461 Tet+ PBMC | Patient 517 CTL clones | Patient 517 Tet+ PBMC | Patient 520 CTL clones | Patient 520 Tet+ PBMC |
|---|---|---|---|---|---|---|---|---|---|---|---|---|
| VB1 | | | | | 1 | 1% | | 7% | 1 | 8% | 1 | |
| VB2 | | | | | | | 1 | 5% | | 3% | 1 | |
| VB3 | 2 | 3% | 2 | | | | 2 | 16% | 1 | | 10 | |
| VB5.1 | 1 | | | | | | | | | 5% | | |
| VB7 | | | | | | | | 3% | 2 | 5% | | |
| VB8 | 7 | 5% | 1 | 4% | | | | | 1 | | 4 | 4% |
| VB9 | 1 | nt | nt | nt | nt | nt | nt | nt | nt | nt | nt | nt |
| VB12 | 2 | 2% | | | | | | | | 5% | | |
| VB13.1 | 1 | 2% | | 4% | | | | 2% | | 14% | 5 | 11% |
| VB13.6 | | 1% | | | | | | 7% | | 7% | | |
| VB14 | 6 | 17% | 44 | 24% | | | 4 | 13% | 1 | 8% | 8 | 9% |
| VB16 | | | | | | | | | | 2% | 1 | 1% |
| VB17 | 7 | 11% | 33 | 37% | 10 | 86% | | 3% | | 6% | 8 | 4% |
| VB20 | 1 | 1% | | | | | | 5% | | | | |
| VB21.3 | 12 | 4% | 2 | 2% | | | | | | | | |
| VB22 | | | | | | | | | | 3% | 1 | |
| VB23 | 1 | | | | | | | | | | 2 | 3% |
| VB? | 17 | | 3 | | | | 3 | | 3 | | 7 | |
| Total: | 61 | 46% | 85 | 72% | 11 | 87% | 10 | 61% | 9 | 66% | 48 | 32% |

TABLE 1-continued

CTL clones established from each patient represent a random selection from the tetramer-reactive CD8+ parent population.

| TCR VB family | [a]Patient 422 | | Patient 476 | | Patient 132 | | Patient 461 | | Patient 517 | | Patient 520 | |
|---|---|---|---|---|---|---|---|---|---|---|---|---|
| | [b]CTL clones | [c]Tet+ PBMC | CTL clones | Tet+ PBMC | CTL clones | Tet+ PBMC | CTL clones | Tet+ PBMC | CTL clones | Tet+ PBMC | CTL clones | Tet+ PBMC |

[a]Clonal CTL lines were established from each patient
[b]Number of clonal CTL lines from each patient expressing the same The same TCR VB chain.
[c]Percent of tetramer-reactive CD8+ T cells in each patient expressing the indicated TCR VB chain.

Up to 85% of sorted cells expanded in various sorts. Randomly selected expanding clones and the tetramer+ population from which they were derived were examined for TCR V-beta expression using TCR V-beta-specific monoclonal antibodies. Peptide specificity and CD8 expression of each clone was confirmed by staining with tetramers and anti-CD8 mAb (data not shown). To obtain an accurate reflection of the total T cell population detected with tetramer in each patient, we decided to rigorously examine at least one representative clone for each subpopulation expressing a different TCR V-beta (Table 2).

Multiple clones were analyzed to determine dominating populations. Clones with unknown TCR V-beta expression (not reactive with any of the anti-TCR V-beta mAb) were also included in the analysis (Table 2). From patients 132, 517 and 461, for which fewer clones were generated, all clones were included in analysis (Table 2).

To determine the effectiveness of tumor lysis by the different TAA-specific T cell clones that were propagated, clones were analyzed for their ability to lyse melanoma cell lines mel 526 and Malme-3M. Both express gp100 and MART-1 melanoma associated antigens and are HLA-A*0201 positive while the third line, A-375, does not express either gp100 or MART-1 and served as a control for antigen-specific killing. In addition, each CTL clone was examined for antigen specific lysis of T2 cells pulsed with high levels (1 µg/ml) of G209-2M or M26 peptides. "Efficient lysis" in these experiments was set at 40% or more specific release of radiolabel from the target cells. 10% or less specific release was categorized as "poor or no lysis", and 10% to 40% was termed "intermediate lysis". All but two of the CTL clones elicited from endogenous anti-tumor responses (from patients 132 and 461) exhibited "efficient lysis" of both the mel 526 and Malme-3M melanoma cell lines (FIG. 2a). In contrast, only a few clones from the vaccine-elicited responses (from patients 422, 476, 520 and 517) efficiently lysed melanoma cells. The majority of clones examined from these vaccine-elicited responses either failed to lyse melanoma targets altogether or lysed them with intermediate efficiency (FIG. 2a). This lack of efficiency in melanoma cell lysis was not due to cellular dysfunction since each clone efficiently lysed T2 cells pulsed with high levels of relevant, but not irrelevant, peptide (FIG. 2a). Overall, the majority of clones derived from endogenous anti-tumor responses (patients 132 and 461) lysed both mel 526 and Malme-3M melanoma target cells more efficiently compared to clones from vaccine-elicited responses (patients 422, 476, 520 and 517), FIG. 2b. These findings show that TAA-specific T cells elicited by heteroclitic peptide vaccination have different tumor-cytolytic potentials from those which develop endogenously.

TABLE 2

CTL clones from each patient selected for functional analysis.

| Patient 517 | | | Patient 520 | | | Patient 461 | | | Patient 422 | | |
|---|---|---|---|---|---|---|---|---|---|---|---|
| Clone: | [a]TCR VB: | [b]Assay: | Clone: | TCR VB: | Assay: | Clone: | TCR VB: | Assay: | Clone: | TCR VB: | Assay: |
| 517.1 | VB7 | M | 520.17 | VB14 | MR | 461.4 | VB2 | MR | 2A12 | VB5.1 | MR |
| 517.2 | VB? | MR | 520.21 | VB14 | MR | 461.8 | VB3 | MR | 2C1 | VB14 | M |
| 517.3 | VB1 | MR | 520.20 | VB3 | MR | 461.9 | VB14 | MR | 2E1 | VB? | MR |
| 517.7 | VB7 | MR | 520.24 | VB3 | MR | 461.10 | VB3 | MR | 3H3.1 | VB20 | MR |
| 517.11 | VB14 | MR | 520.30 | VB17 | MR | 461.17 | VB14 | MR | 4A6 | VB9 | MR |
| 517.13 | VB3 | MR | 520.32 | VB17 | MR | 461.21 | VB? | MR | 4F1 | VB1 | MR |
| 517.14 | VB8 | MR | 520.22 | VB? | MR | 461.24 | VB14 | MR | 5F9 | VB8 | MR |
| 517.16 | VB? | MR | 520.31 | VB? | MR | 461.25 | VB14 | MR | 1A12 | VB21.3 | M |
| 517.40 | VB? | MR | 520.33 | VB? | MR | 461.29 | VB? | MR | 422.T1 | VB13.1 | MR |
| | | | 520.38 | VB? | MR | 461.30 | VB? | MR | 422.23 | VB14 | M |
| | | | 520.41 | VB? | MR | | | | 422.50 | VB14 | MR |
| | | | 520.55 | VB? | MR | | | | 422.47 | VB17 | MR |
| | | | 520.16 | VB8 | MR | | | | 422.66 | VB17 | M |
| | | | 520.18 | VB16 | MR | | | | 422.27 | VB12 | MR |
| | | | 520.19 | VB13.1 | MR | | | | 422.49 | VB3 | MR |
| | | | 520.43 | VB2 | MR | | | | 3F2 | VB? | MR |
| | | | 520.49 | VB23 | MR | | | | 2H9 | VB? | MR |
| | | | 520.52 | VB1 | MR | | | | 4E2 | VB? | MR |
| | | | 520.59 | VB22 | MR | | | | 3H3.2 | VB? | MR |
| | | | | | | | | | 422.64 | VB8 | M |
| | | | | | | | | | 422.72 | VB3 | M |

TABLE 2-continued

CTL clones from each patient selected for functional analysis.

|  |  |  | 422.T8 | VB1 | M |
| --- | --- | --- | --- | --- | --- |
| Patient 476 | | | Patient 132 | | |
| Clone: | TCR VB: | Assay: | Clone: | TCR VB: | Assay: |
| 476.101 | VB14 | MR | 132.1 | VB17 | MR |
| 476.102 | VB14 | M | 132.2 | VB17 | MR |
| 476.105 | VB14 | MR | 132.3 | VB17 | M |
| 476.108 | VB14 | MR | 132.4 | VB17 | M |
| 476.133 | VB14 | M | 132.5 | VB17 | M |
| 476.104 | VB17 | MR | 132.6 | VB1 | MR |
| 476.125 | VB17 | MR | 132.9 | VB17 | M |
| 476.137 | VB17 | M | 132.10 | VB17 | M |
| 476.139 | VB17 | M | 132.11 | VB17 | M |
| 476.140 | VB17 | M | | | |
| 476.15 | VB21.3 | MR | | | |
| 476.110 | VB3 | MR | | | |
| 476.N11 | VB3 | M | | | |
| 476.25 | VB8 | MR | | | |
| 476.N8 | VB? | MR | | | |
| 476.28 | VB? | MR | | | |
| 476.114 | VB? | MR | | | |
| 476.26 | VB21.3 | M | | | |

[a]The TCR VB usage of each CTL clone was determined using a panel of 19 anti-VB mAbs by flow cytometry.
[b]All lines selected for functional analysis were assayed for lysis of melanoma cells (M). Some lines were also subjected to RE analysis (MR).

Figure 3A:
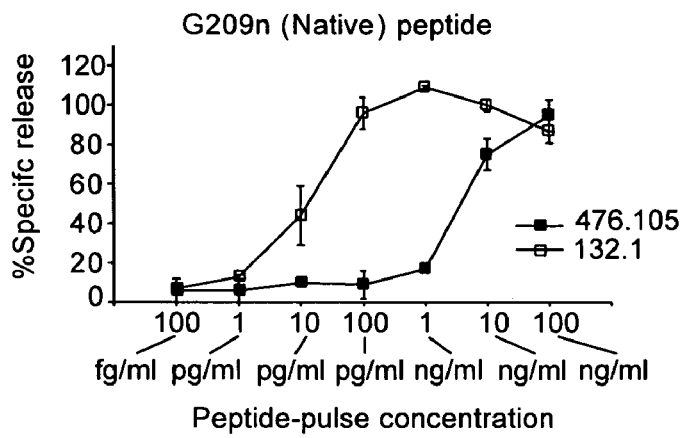
FIGS. 3A-3J. Endogenous CTL clones have higher RE than vaccine-elicited CTL clones. CTL clones representing different tetramer+ populations in each patient expressing different V-beta, were assayed for lysis of T2 cells pulsed with various dilutions of G209n, G209-2M, M27, or M26 peptides in $^{51}$Cr-release cytotoxicity assays. All assays were performed in triplicate and each clone was assayed twice. Error bars reflect variation between two separate assays. 3a.-c. CTL clones 476.105 and 132.1 were assayed for lysis of T2 cells pulsed with 10-fold dilutions of a. native or c. heteroclitc peptide at concentrations ranging from 100 fg/ml to 100 ng/ml. b. CTL clones 476.105 and 132.1 were assayed for lysis of Malme-3M melanoma cells. d.-e. RE scores, equal to the negative $\log_{10}$ of the peptide concentration that resulted in 40% lysis of peptide-pulsed T2 cells, for both (d.) MART-specific and (e.) gp100-specific clones from all patients were correlated with efficiency in lysing melanoma cells. Correlation coefficients were 0.66 for MART-specific clones and 0.81 for gp100-specific clones. f.-i. Endogenous (461 and 132) and vaccine-induced (517, 520, 422 and 476) CTL clones were compared for RE in lysing target cells. f-g. Target cells were pulsed with native peptides (f.) M27 and (g.) G209n. Mean RE (weighted) for each response is indicated with horizontal bars. Weighted means were based on all clones, not only those assayed, and were estimated by summing the RE of each analyzed clone multiplied by the number of total clones expressing the same V-beta in each patient. Weighted means were: 517: 5.7; 520: 7.0; 461: 7.9; 422: 9.7; 476: 9.9; and 132: 11.2. One-tailed T-tests demonstrated that endogenous CTL had significantly higher RE than vaccine induced CTL: 461 vs 517: $p=1.8\times10^{-5}$; 461 vs 520: $p=1.1\times10^{-3}$; 132 vs 422: $p=6\times10^{-6}$; and 132 vs 476: $p=4.3\times10^{-4}$. h.-i. Target cells were pulsed with heteroclitic peptides (h.) M26 and (i.) G209-2M. j. CTL clones that were efficient (132.2 and 476.104) or inefficient (422.5F9 and 476.108) in melanoma lysis were compared for lysis of target cells pulsed with increasing concentrations of native or heteroclitic peptides (as in a. and c.).
Figure 3B:
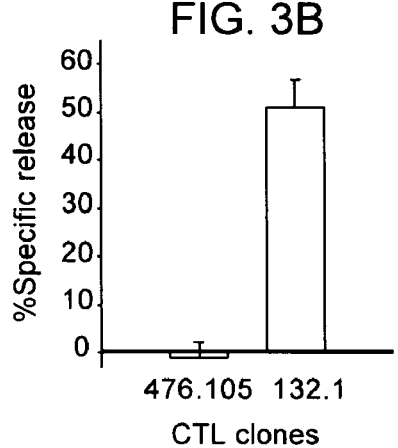
Figure 3C:
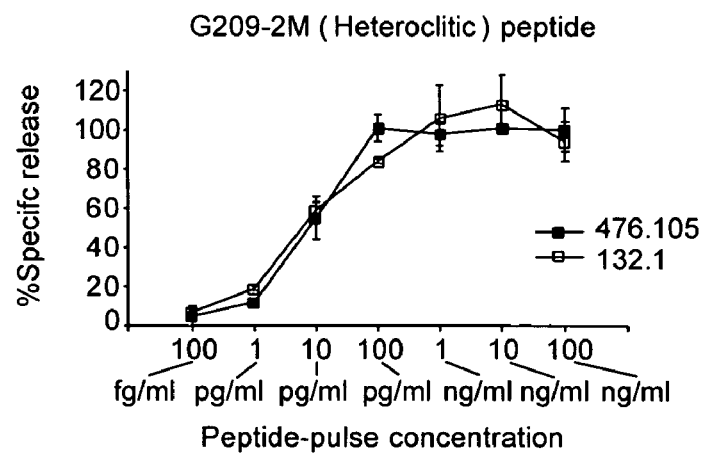

D. RE for native and heteroclitic peptides of T cells from endogenous or vaccine-elicited responses. We hypothesized that CTL clones that did not efficiently lyse melanoma targets may be incapable of recognizing the relatively low surface densities of native peptide present on tumor cells. CTL clones selected for analysis of tumor lysis were also assessed for RE for the native and heteroclitic peptides via a 10 log range of dilutions. This is illustrated with clones 132.1 and 476.105 (FIG. 3a). There were considerable differences in killing of peptide-pulsed T2 cells by these two clones. The relative differences in RE for G209n native peptide displayed by the two clones highlighted in FIG. 3a correlated with their ability to lyse melanoma cells: the high RE clone 132.1 efficiently lysed melanoma targets whereas the low RE clone 476.105 did not (FIG. 3b). In contrast to the differences in RE for G209n peptide, similar assays revealed little difference in RE of the two clones for G209-2M heteroclitic peptide (FIG. 3c), showing that these clones recognize the native and heteroclitic peptides differently, and that RE for the native, but not heteroclitic, peptide correlates with tumor-lytic potential.

Figure 3D:
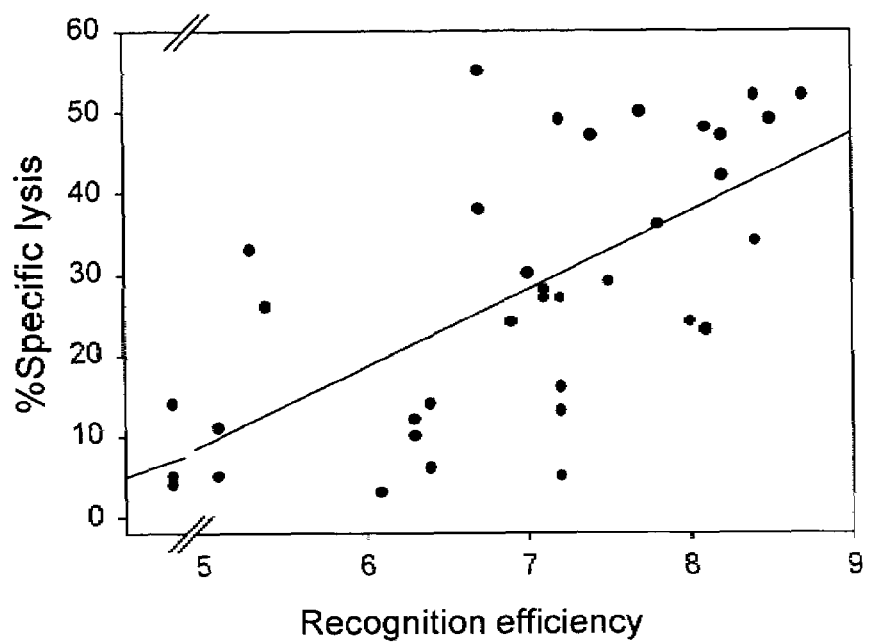
Figure 3E:
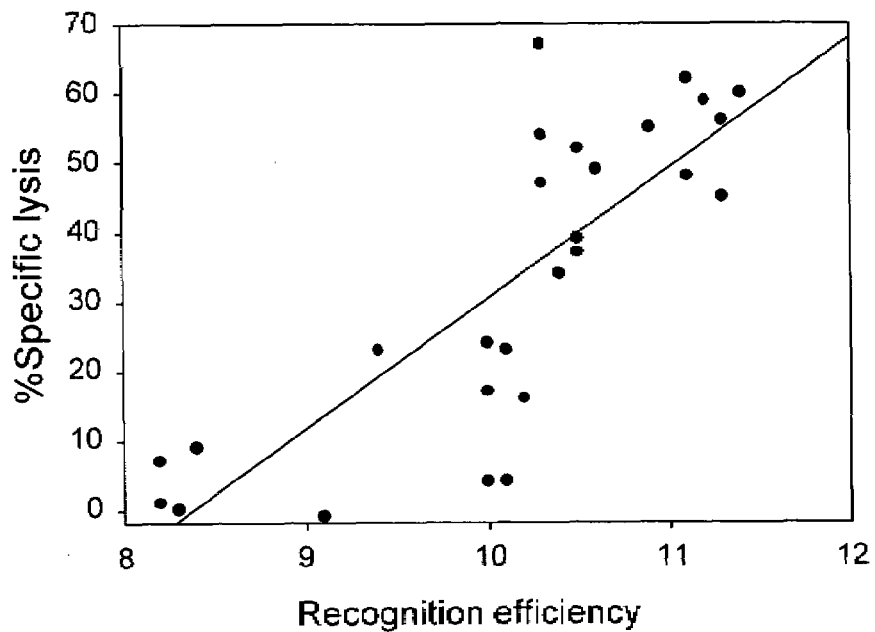
Figure 3F:
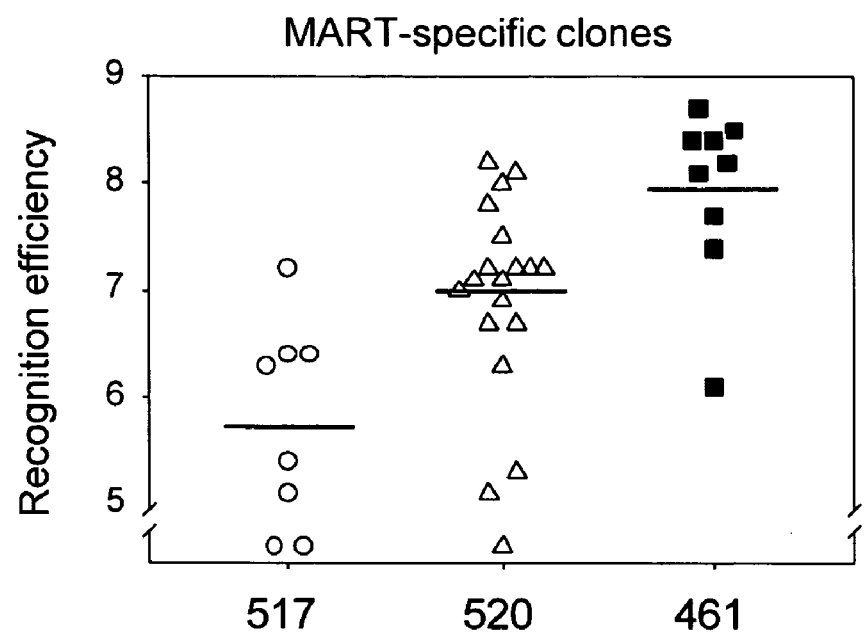
Figure 3G:
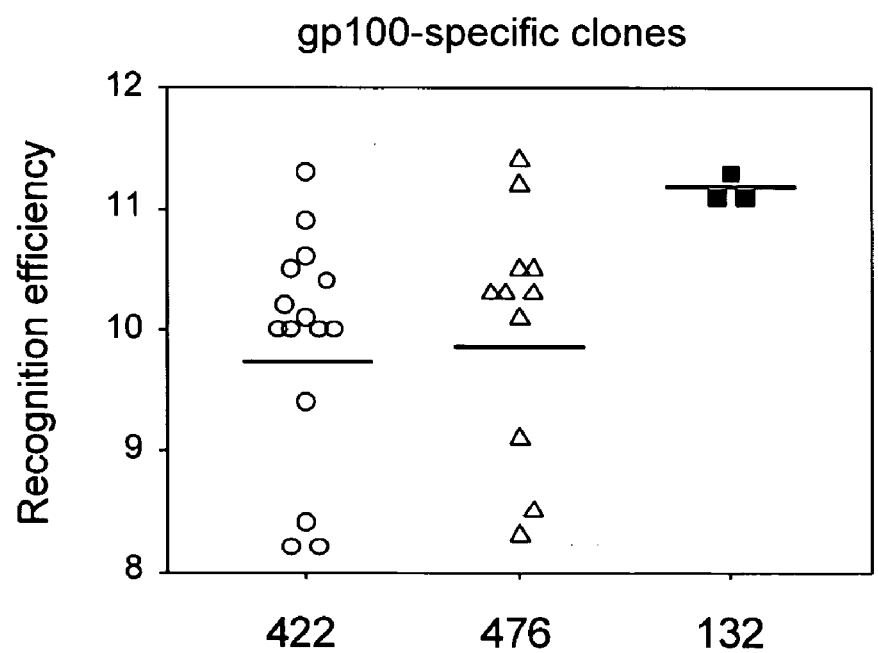
Figure 3H:
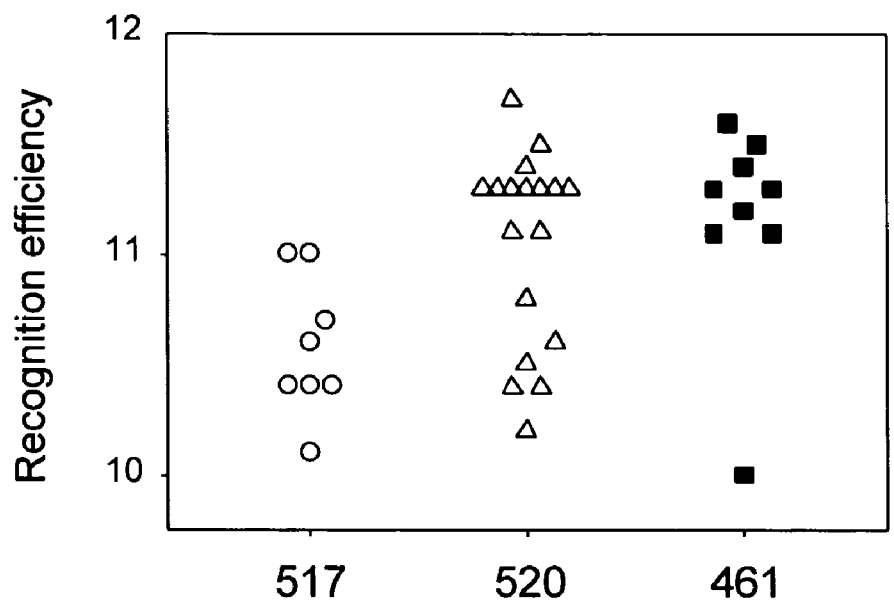
Figure 3I:
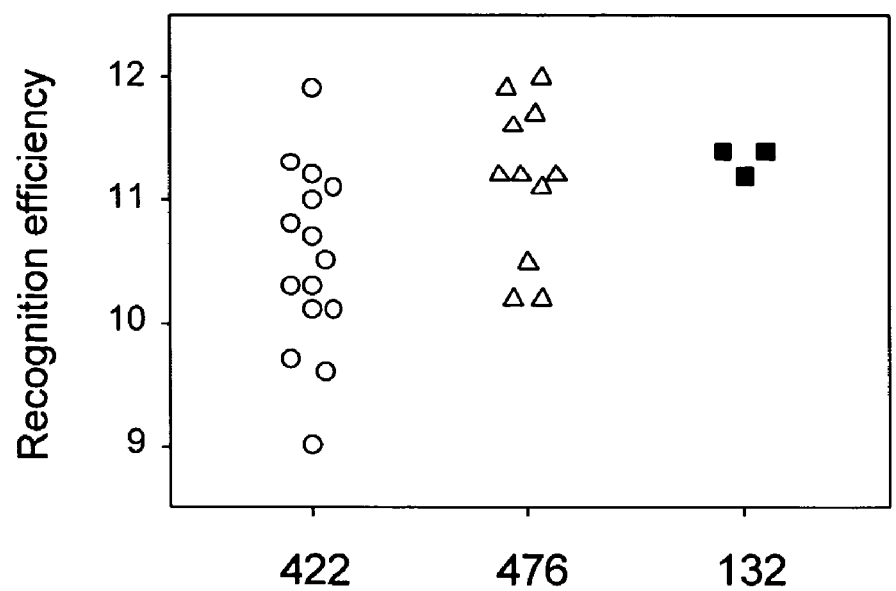

Similar RE assays were performed for the remaining clones from each patient selected for analysis. In order to compare REs of various CTL lines, each clone was assigned an RE score expressed as the negative log10 value of the peptide concentration required for 40% percent specific lysis at an E:T ratio of 10:1. For clones 132.1 and 476.105 these scores were 11.1 and 8.3 for assays with G209n peptide (FIG. 3a), and 11.2 and 11.2 for assays with G209-2M heteroclitic peptide (FIG. 3c), respectively. We compiled the data on clones from all patients, which showed a strong correlation between tumor-lytic potential and RE for native peptide (FIGS. 3d and e). Overall, clones generated from endogenous anti-tumor responses had much higher RE for the native peptide than clones generated from post-vaccine responses (FIGS. 3f and g). We estimated the composite RE of the overall TAA-specific response (composed of a heterogeneous population of T cells) in vivo by summing the RE of each clone multiplied by its representation in the original mixture (the representation was estimated based on the proportion of TAA-specific cells expressing the same V-beta as the clone). These are represented as horizontal bars for each response. Clearly, the endogenous responses (461 and 132) had a higher overall, and more homogeneous, RE for the native peptide than the vaccine-elicited responses (422, 476, 517, 520), FIGS. 3f and g. Importantly, the vaccine-elicited clones also exhibited wide variations in RE for the heteroclitic peptide as compared to the endogenous clones (FIGS. 3h and i). These findings show that the variation in RE for native peptides, and hence ability to lyse tumor, for vaccine-elicited CTLs is not merely a reflection of differential recognition of native and heteroclitic peptides by many clones. Rather, variations in RE are a function of the manner in which these cells were elicited by vaccination.

Figure 3J:
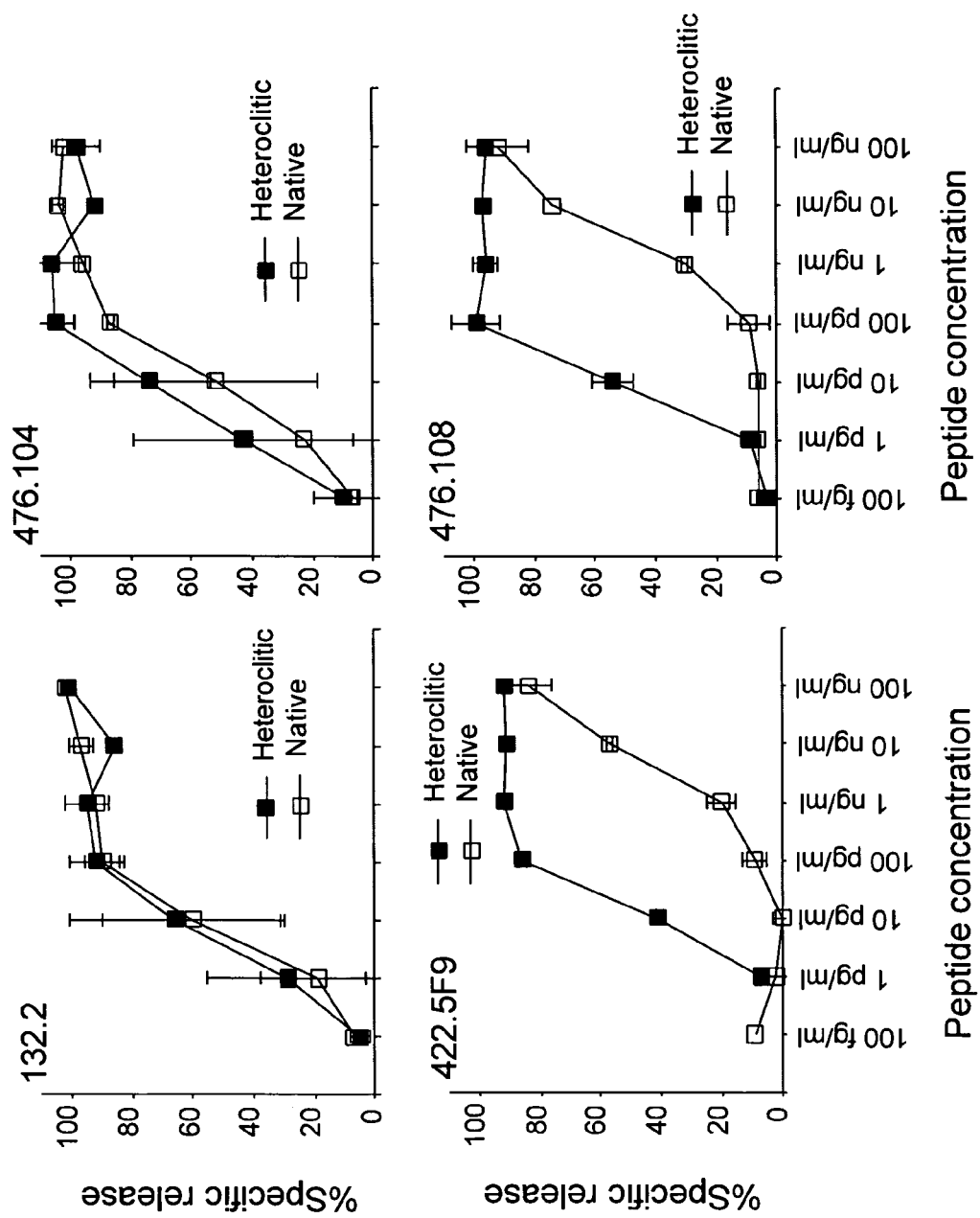

Many clones recognized native and heteroclitic peptides differently, such as 422.5F9 and 476.108 (FIG. 3j). These clones failed to lyse tumor targets (FIG. 2a). In contrast, some clones, such as 132.2 and 476.104, recognized heteroclitic and native peptide with similar efficiency (FIG. 3j) and efficiently lysed tumor cells (FIG. 2a). Many clones were also generated which had low RE for both native and heteroclitic peptides and were inefficient in tumor lysis.

Figure 4B:
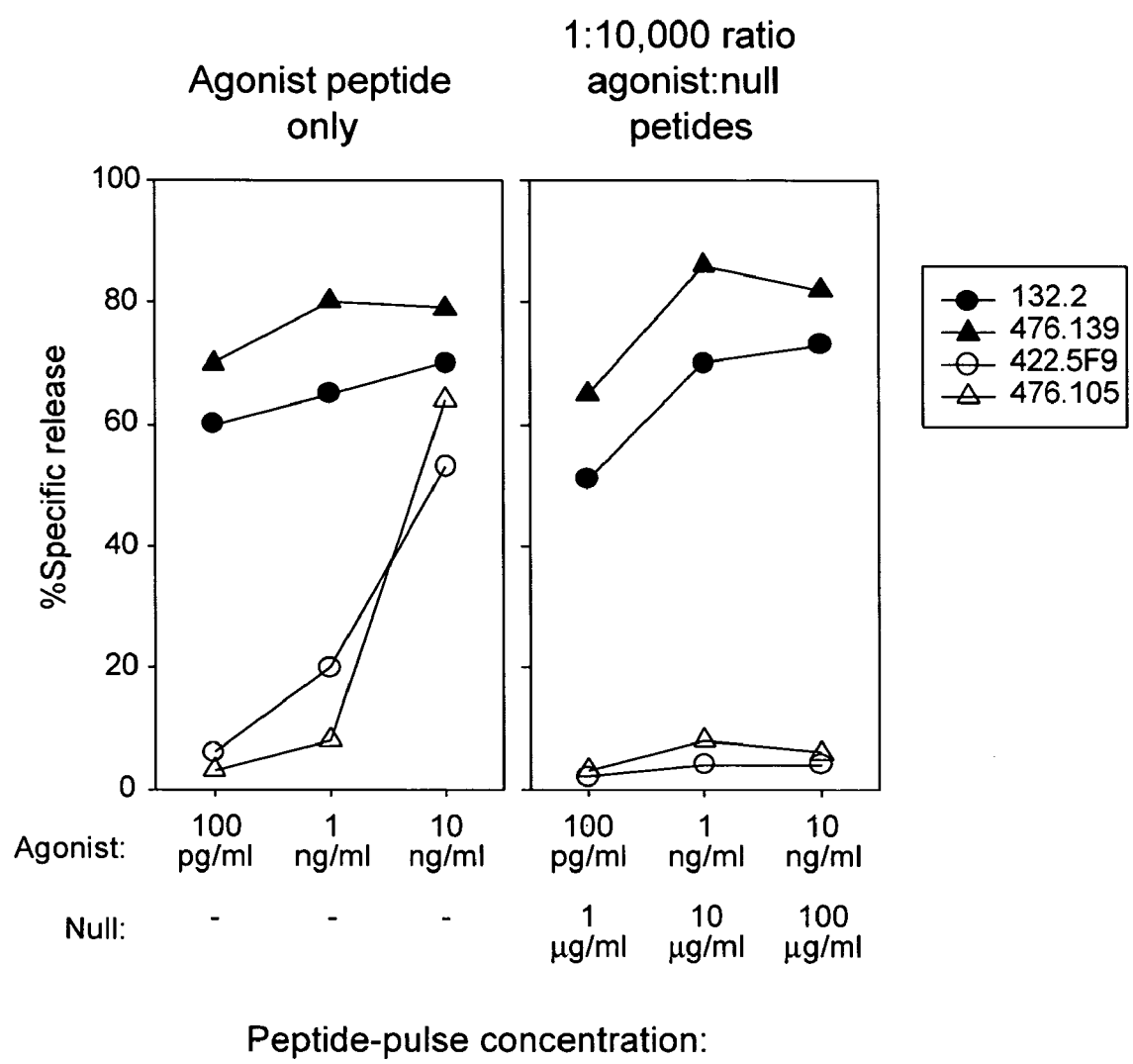

E. Selective stimulation of high RE T cells with peptide mixtures. To develop a vaccine strategy which may selectively stimulate T cells of high RE in vivo, we devised a novel strategy in which an agonist peptide is mixed with an analogue peptide with null activity and similar HLA binding affinity. G209-3A represents such an analog for G209. This analog peptide, which differs from the native peptide by a substitution of an asparagine for an alanine at residue 211, has similar affinity to HLA-A2.1 as the native peptide but does not activate G209-specific target cell lysis by T cell clones at any concentrations (data not shown). When G209n and G209-3A peptides were combined at various ratios for pulsing of T2 target cells, we found that a 1:10,000 ratio of native to null peptide abolished lysis of T2 cells by low RE CTl clones but lysis by high RE CTL clones was preserved (FIG. 4a). Importantly, this effect was observed with a wide range of peptide concentrations spanning at least two logs (FIG. 4b), showing that high RE CTL clones may be selectively stimulated using such a strategy across a broad range of physiologically achievable peptide concentrations in vivo.

III. Discussion

To achieve maximal clinical responses, the majority of T cells elicited by vaccination in cancer patients should be capable of lysing tumor targets. We have undertaken the most detailed analysis to-date, on a single cell level, of cytolytic T cell responses elicited by cancer vaccination and compared these with endogenous anti-tumor CTL responses. CTL clones were selected directly from patient PBMC samples without enrichment in culture to closely reflect the composition of the antigen-specific T cell response in vivo at the time of isolation. Our data revealed that T cell populations induced by vaccination were strikingly different from endogenous populations: while some CTL elicited by vaccination could kill melanoma targets, most were inefficient in tumor cell lysis. In contrast, nearly all CTL clones from endogenous responses were efficient at melanoma cell lysis. This difference was directly related to RE. Clones that did not lyse tumor cells required up to $10^3$-fold higher concentration of peptide for similar levels of lysis of T2 targets compared to T cell clones that were tumor-lytic. Side-by-side comparison of endogenous CTL and vaccine-induced CTL suggested that the activation of low RE TAA-specific CTL was selectively driven by heteroclitic peptide vaccination. Thus, high doses of peptide and/or the higher levels of expression of heteroclitic peptide on APC may induce and actively propagate predominantly T cells with too low RE for recognition of physiological levels of the native peptide present on tumor targets. These data show an inverse relationship between antigen density and the RE of T cells elicited.

Differential recognition of native and heteroclitic peptides by many T cells may also account for the induction of non-tumor-lytic CTL clones by heteroclitic peptide vaccines. However, our data suggest that epitope density may be the dominant driving factor for RE in vivo. In all of the vaccine-elicited T cell responses, many of the T cells generated were either of low or intermediate RE not only for the native peptide, but also for the heteroclitic peptide, and exhibited no or intermediate lysis of tumor targets. In contrast, nearly all of the clones generated from the endogenous responses were of high RE. This finding shows that the high dosage of peptides administered in vaccinations and the increased binding capacity of heteroclitic peptides to MHC molecules—the very quality that provides them with increased immunogenicity—drive the induction of many T cells with low RE for both heteroclitic and native peptides.

Another implication of this study is that the number of cells measured by current methods, including ELISPOT or staining with MHC tetramers, may not correlate directly with the RE or tumor-cytolytic potential of T cell responses to vaccination. For example, of the nine clones analyzed from patient 517, none were efficient in tumor cell lysis, yet these cells were detectable by MHC tetramer staining. T cells with low RE for native TAA do not efficiently lyse tumor, and therefore are unlikely to have an impact on clinical outcome. Furthermore, it may be possible that low RE TAA-specific T cells may interfere with elicitation of high RE T cells either by direct competition for antigen on APC surface or down-modulation of peptide-MHC complexes.

Our data show that not only quantity, but quality, of the T cell response elicited by vaccination is critical to clinical efficacy. To selectively activate T cells of high RE, we developed a novel approach in which T cells are stimulated with a combination of agonist and null peptides. By combining peptides with similar HLA binding properties, there is no selective advantage in APC uptake between peptides, hence the ratios would be preserved. We showed that at certain ratios, there is a wide dynamic range of peptide concentrations at which high RE T cells are selectively activated over low RE T cells. This approach circumvents the unpredictable nature of peptide trafficking and uptake in APC. Furthermore, this strategy mimics what naturally arises from tumor cells in vivo: APC that phagocytize apoptotic tumor cells present a vast mixture of peptides—cognate peptides likely exist with a vast excess of null peptides. This may be the mechanism by which high RE T cells are selectively expanded in endogenous responses, and our novel vaccination strategy may replicate this natural mechanism of RE selection in vivo.

In certain embodiments, a complete vaccination strategy will involve an initial induction phase, followed by progressive shaping of the response to higher RE. Although heteroclitic peptide vaccination may drive T cells of mixed high and low RE, such a strong stimulus is desirable in certain instances to induce an initial de novo T cell response. Thus, naïve TAA-specific T cells, with inadequate RE to become activated by low densities of native peptides present on tumor cells, may become efficient in tumor lysis upon vaccination with heteroclitic peptide. Therefore, optimized use of heteroclitic peptide to induce an initial peptide-specific T cell response, followed by selective expansion of the highest RE tumor-lytic T cells using combinations of native and analog peptides, according to the present invention, is a particularly effective strategy with clear clinical application in certain embodiments.

In summary, we have demonstrated that vaccination with heteroclitic peptide at high concentrations drives T cell responses of predominantly low RE, and that only high RE T cells are effective at lysing tumor. This may be a key factor in the lack of correlation between immunological and clinical responses after vaccination. Importantly, the situation is distinctly different in endogenous responses, in which the CTLs generated are predominantly of high RE. This suggests that the manner in which T cells are elicited is different in these two settings and underlie their differences biologically. The present invention provides a novel modification of peptide vaccine strategy that preserves the initial immunogenic properties of heteroclitic peptide vaccination while selectively expanding high RE T cells. Such a strategy significantly improves the efficacy of cancer vaccination therapies.

It is apparent from the above results and discussion that the subject invention provides convenient protocols for producing high RE cytolytic cells. Accordingly, the subject invention is capable of producing cells that are truly cytolytic for a target cell as it naturally occurs, and not just a cell pulsed with the target peptide. As such, the subject invention represents a significant contribution to the art.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to

SEQUENCE LISTING

<160> NUMBER OF SEQ ID NOS: 4

<210> SEQ ID NO 1
<211> LENGTH: 9
<212> TYPE: PRT
<213> ORGANISM: syArtificial Sequence
<220> FEATURE:
<223> OTHER INFORMATION: synthetic peptide

<400> SEQUENCE: 1

Ile Thr Asp Gln Val Pro Ser Phe Val
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Ile Thr Ala Gln Val Pro Ser Phe Val
1               5

<210> SEQ ID NO 3
<211> LENGTH: 10
<212> TYPE: PRT
<213> ORGANISM: Artificial Sequence
<220> FEATURE:
<223> OTHER INFORMATION: synthetic peptide

<400> SEQUENCE: 3

Glu Leu Ala Gly Ile Gly Ile Leu Thr Val
1               5                   10

<210> SEQ ID NO 4
<211> LENGTH: 9
<212> TYPE: PRT
<213> ORGANISM: Artificial Sequence
<220> FEATURE:
<223> OTHER INFORMATION: synthetic peptide

<400> SEQUENCE: 4

Ile Met Asp Gln Val Pro Ser Phe Val
1               5

The invention clamed is:

1. A method of producing tumor cell-reactive T-lymphocytes, said method comprising:
contacting a lymphocyte population with an effective amount of a peptide mixture comprising a native agonist peptide from a tumor-associated antigen, wherein the agonist peptide comprises the amino acid sequence (SEQ ID NO:1) ITDQVPSFV and an analog peptide that comprises the sequence (SEQ ID NO:2) ITAQVPSFV;
to produce T-lymphocytes reactive for said tumor cell.

* * * * *

UNITED STATES PATENT AND TRADEMARK OFFICE
CERTIFICATE OF CORRECTION

| | | |
|---|---|---|
| PATENT NO. | : 7,598,223 B2 | Page 1 of 1 |
| APPLICATION NO. | : 11/185245 | |
| DATED | : October 6, 2009 | |
| INVENTOR(S) | : Lee et al. | |

It is certified that error appears in the above-identified patent and that said Letters Patent is hereby corrected as shown below:

Column 1:

• Please replace lines 14-17 with:

-- This invention was made with Government support under contract CA090809 awarded by the National Institutes of Health. The Government has certain rights in this invention. --

Signed and Sealed this
Fifth Day of April, 2011

David J. Kappos
*Director of the United States Patent and Trademark Office*